United States Patent [19]
Aoshima

[11] Patent Number: 5,811,287
[45] Date of Patent: Sep. 22, 1998

[54] BIOLOGICALLY PURE BACILLUS BADIUS FERM BP-4493 HAVING DEODORIZING ACTIVITY

[75] Inventor: Mutsumi Aoshima, Shizuoka, Japan

[73] Assignee: Asahi Kasei Kogyo Kabushiki Kaisha, Osaka, Japan

[21] Appl. No.: 652,575

[22] PCT Filed: Dec. 12, 1994

[86] PCT No.: PCT/JP94/02079

§ 371 Date: Jun. 26, 1996

§ 102(e) Date: Jun. 26, 1996

[87] PCT Pub. No.: WO95/16769

PCT Pub. Date: Jun. 22, 1995

[30] Foreign Application Priority Data

Dec. 13, 1993 [JP] Japan .................................. 5-312082

[51] Int. Cl.⁶ .................. C12N 1/00; C12N 1/20

[52] U.S. Cl. .................. 435/252.5; 435/252.31; 435/832

[58] Field of Search .............. 435/252.31, 252.5, 435/832

[56] References Cited

FOREIGN PATENT DOCUMENTS 61-78352 4/1986 Japan .
1-144971 6/1989 Japan .

*Primary Examiner*—David M. Naff
*Assistant Examiner*—Deborah K. Ware
*Attorney, Agent, or Firm*—Young & Thompson

[57] ABSTRACT

A pure cultured microorganism of a *Bacillus badius* MA001 (FERM BP-4493) strain having deodorant and sporogenic properties. A microbial composition containing the same as the active ingredient and a method of deodorizing offensive odor sources with the composition. The order sources include fatty acids of approximately 1 to 10 carbon atoms, ammonia, indole, skatole and trimethylamine.

3 Claims, 2 Drawing Sheets

BIOLOGICALLY PURE BACILLUS BADIUS FERM BP-4493 HAVING DEODORIZING ACTIVITY

FIELD OF THE INVENTION

The present invention relates to a substantially pure cultured microorganism of *Bacillus badius* MA001 (FERM BP-4493) strain having deodorant and sporogenic properties, a microorganism composition containing the substantially pure cultured microorganism of *Bacillus badius* MA001 strain having deodorant and sporogenic properties as the active ingredient, and a deodorizing method using the said mirorganism composition.

PRIOR ARTS

A deodorizing method by decomposing offensive odor sources by the use of specific microorganisms, i.e. microbial deodorizing method, has been developed by means of the recent biotechnology. A deodorizing process in the microbial deodorizing method is based on the decomposition of odorous substance from offensive odor sources. At present, soil deodorizing method is developed as an application of microbial deodorizing method. This is a deodorizing system for decomposing offensive odorous substance by an action of soil microorganisms in soil after discharging the collected odor which is blown into pipes set in the soil.

Microbial deodorizing method in which odorous gas is blown into a column packed with immobilized microbial carrier, has also been developed. Examples of the carrier are sawdust, peat moss and rock wool. In the operation of these deodorizing methods, there are so many problems, for example constant water spray and pH adjustment are essential and require the high cost on maintenance of the soil and carrier. Catching the offensive odor is practically quite troublesome and gathering offensive odorous gas requires high cost which necessitate the construction of large scale plants. Furthermore treatment capacity has to be limited due to high loading in the treatment.

Microorganisms which act as microbial deodorant are generally soil bacteria, therefore deodorizing effects are different depending on the soil used and type of odor substances. For obtaining practically sufficient deodorizing effects, one to several months for adaptation of offensive odor substances are necessary and in that case constant stable operation can not be expected. Adaptation by offensive odor result in the growth of specific soil bacteria and generation of ammonia. In this case, bacteria which do not generate excess ammonia are essentially required.

Mechanisms of deodorizing action by soil bacteria are mostly unknown, and are generally recognized as a cleaning up action of soil bacteria. Few reports are known in relation to the deodorizing action of single or multiple microorganisms. Reports on the studies in view of microbial action are not so many. Major studies on microorganisms which decompose organic sewage and offensive odorous substance are conducted on the sewage treatment by activation sludge method. Studies on the properties of microorganisms which decompose offensive odorous substance and decomposition process are in progress.

Deodorant containing specific microorganism, especially in the case that offensive odorous composition is sulfur compound, is reported, for example *Thiobacillus thioparus* which deodorizes methyldisulfide [FEMS Microbiology Letters, 34 (1986) 13–19] and Pseudomonas which decomposes hydrogen sulfide (Japan. Pat. Unexam. Publ. No. 4-262778). Acinetobacter calcoacetius which can decompose indole and skatole and a microbial decomposition of indole and skatole are known (Japan. Pat. Unexam. Publ. No. 2-53482). Decomposing offensive odorous substance by use of single microorganisms are limited due to practically complex offensive odor and the deodorizing effects can not be expected. These microorganisms in the deodorant are not stable for long term, and maintaining vaiable counts of microorganisms in the offensive odor source are difficult.

Microorganisms which decompose indole and skatole such as Bacillus sp. ID246 and a biological decomposition of indole and skatole have been known (Japan. Pat. Unexam. Publ. No. 2-53481). A microorganism belonging to Bacillus has an activity for decomposing specific offensive odor such as indole and skatole, however deodorized offensive odor is limited and deodorizing activity is not so effective. The disclosed strain Bacillus sp. ID246 is not *Bacillus badius* because of its biochemical properties such as utilization of sugar, therefore it is different from *Bacillus badius* of the present invention.

Deodorization of feces by fermentation in use of microorganisms such as *Bacillus subtilis, Bacillus fluorescens liquefaciens, Bacillus mesenterlcus vulgatus* and *Bacillus mycoides* is known (Japan. Pat. Unexam. Publ. No. 52-86273). These microorganism strains have, however, not been deposited and no disclosure has been made, and reexamination for confirming the activities of these microorganisms cannot be made. In the present invention, however, fermentation process is not required, therefore taxonomical properties of *Bacillus badius* of the present invention is different from those microorganisms.

Animal feeds and disposal of animal waste in use of multiple microorganisms including *Aspergillus oryzae, Rhizopus delmar, Aspergillus niger, Mucor miehei* and *Aspergillus fumigatus* are known (Japan. Pat. Unexam. Publ. No. 57-180498). Deodorant mixed with microorganisms including Bacillus, nitrifying bacterial, nitrite bacteria, Aspergillus and Pseudomonas is also known (Japan. Pat. Unexam. Publ. No. 1-262998). This deodorant use of multiple microorganims has difficulty with maintaining stable population of each microorganism, therefore deodorizing effect is not stable.

Offensive odor of excretions from livestock and poultry such as cattle, pigs and chickens and pets such as dogs and cats causes troubles. In order to solve these problems, the offensive odor is tried to be removed by spraying reodorant over excretions, and many types of deodorants have been developed. In such deodorizing process, deodorants should be sprayed over whole surface of the offensive odor sources for expecting complete deodorization. This should have been done in any time of excretions and whole area of the cages and breeding farms. In practical rearing, sources of offensive odor distributed in a wide area around the farms, and deodorization by spraying deodorant requires large scale labor which results in high costs for facilities and maintenance.

Development of the deodorant which is effective by adding in feeds, is expected, however this type of deodorant has not been found in view of effectiveness and safety problems.

PROBLEMS TO BE SOLVED BY THE INVENTION

In recent years, animal industries become specialized and large scale, which cause the offensive odor pollution of the social problems. Consequently, continuance of the animal industries becomes difficult not only in the suburbs but also in the countryside, and countermeasures therefor are needed.

Rearing the pets such as dogs and cats in the room increases social problems caused by offensive odor of their feces and urines.

Serious social problems caused by offensive odor by garbage and sewage from daily livings result in an increase in the complaints.

The present invention has solved those offensive odor pollutions such as putrefaction of the organic substances.

The present invention provides new microorganism which is effective for micorbial deodorization of offensive odor originated from fatty acids of carbon 1–10, ammonia, indole, skatole and trimethylamine or combination thereof, with low cost and high safety, as well as effective for long term treatment and odor of low concentration in the broad area, and a deodorant containing the same as an effective ingredient.

MEANS FOR SOLVING THE PROBLEMS

We have isolated many types of natural microorganisms from soil samples of mountain forests and fields in Tanakayama, Tagata-gun, Shizuoka-ken, Japan. We have also studied properties thereof and found that cultured new microorganism strain MA001 belonging to Bacillus badius (FERM BP-4493) can effectively remove offensive odor substance from feces and urine of livestock and poultry, the origin of offensive odor. The present microorganism having effective deodorizing properties on the offensive odor of feces and urine of livestock and poultry, can catabolize carbon sources, a major offensive odor source, such as $C_{1-10}$ fatty acid consisting of formic acid, acetic acid, propionic acid, n-butyric acid, iso-butyric acid, n-valeric acid, iso-valeric acid, caproic acid and caprylic acid, and nitrogen source such as ammonia. One mililiter of the cultured mass of the present microorganism is diluted with 9 ml of purified water to prepare 10 fold dilution. Two drops of Nessler reagent are added thereto and mixed well. Since the mixture does not become turbid, the cultured mass of the present microorganism shows low concentration of ammonia. Therefore the present microorganism has specific useful properties with effective decomposition of trimethylamine, indole and skatole. The present microorganism strain has sporogenic property, consequently it can maintain high stability in the feed, preparation or rearing fields.

An object of the present invention is to provide substantially pure cultured microorganism of Bacillus badius MA001 (FERM BP-4493) strain having deodorant and sporogenic properties.

Another object of the present invention is to provide a microbial composition containing the substantially pure cultured microorganism of Bacillus badius MA001 (FERM BP-4493) strain having deodorant and sporogenic properties as the active ingredient.

Further object of the present invention is to provide a method of deodorizing offensive odor sources with the microbial composition containing the substantially pure cultured microorganism of Bacillus badius MA001 (FERM BP-4493) strain having deodorant and sporogenic properties as the active ingredient.

A further object of the present invention is to provide a cultured microorganism having deodorant properties with catabolizing or decomposing fatty acid of approximately $C_{1-10}$, ammonia, trimethylamine, indole and skatole which constitute offensive odor substances generated from putrified organic waste such as feces and urine of livestock and poultry, offensive odor from garbage and sewage from daily living and offensive odor in sewage treatment.

Still further object of the present invention is to provide deodorant containing the present microorganism as the active ingredient as well as the method of deodorizing offensive odor sources using the same.

Example of a microorganism having deodorant activity of the present invention is a new microorganism strain Bacillus badius MA001, a non-pathological bacterium having following taxonomical properties. Mutant or variant of the strain can also be mentioned if the deodorizing activity thereof deos not disappear.

The present microbial strain has, as clearly seen in the examples hereinbelow, sporulating activity at humid high temperature with high stability, therefore it is quite stable in the feed and shows deodorizing action by catabolizing and decomposing the offensive odor sources.

Taxonomical properties of the present strain are compared by consulting "Bergey's Manual of Systematic Bacteriology, Vol. 2" and "Manual for the Identification of Medical Bacteria, 2nd Ed. by S. T. Cowan" (Japanese Ed. Kindai Publ. Co.), with type culture strain Bacillus badius IAM 11059, and the following findings are obtained.

Comparison with the taxonomical properties of the present strain MA001 and type culture Bacillus badium IAM 11059 is shown in Table 1: morphorogical findings; Table 2: growth properties in various media; Tables 3 and 4: biochemical properties and Table 5: fermentation of sugar (utilization).

TABLE 1

| Morphological findings | Bacillus badius IAM 11059 | MA001 |
|---|---|---|
| Form of cell | rod | rod |
| Length of cell ($\mu$m) | 4~5 | 3~6 |
| Diameter of cell ($\mu$m) | 0.8~1.2 | 0.8~1.2 |
| Spore | Sporulation | Sporulation |
| Swelling of sporangium | None | None |
| Shape of spore | Oval | Oval |
| Position of spore | Center or edge | Center or edge |

(Note: Morphological observation in culture of aerobic condition at 37° C. for 72 hours in Heart-infusion agar)

TABLE 2

| Medium | Bacillus badius IAM 11059 | MA001 |
|---|---|---|
| DHL agar | no growth | no growth |
| MacConkey agar | no growth | no growth |
| Bouillon agar | Colony; round, elevated convex, smooth to wavy periphery, smooth to rough surface, homogeneous to curly structure, Hardness; fatty, Color: pale yellowish white to pale yellow non-transparent. Good growth in the medium | Colony: round, elevated, convex, smooth to wavy periphery, smooth to rough surface, homogeneous to curly structure, Hardness; fatty, Color: pale yellowish white to pale yellow non-transparent. Good growth in the medium |
| Bouillon broth | No surface growth, yellowish white, homogeneous turbid growth | No surface growth, yellowish white, homogeneous turbid growth |
| Bouillon gelatin | Growth with dish type, slight liquefaction of gelatin | Growth with dish type, no liquefaction of gelatin |
| Litmus milk | | |
| acid production | + | − |
| lab | − | − |
| Blood agar (10% defibrinated blood heart-infusion agar) | | |
| rabbit | Good growth, no hemolysis | No growth |
| sheep | Good growth, no hemolysis | No growth |
| horse | Good growth, no hemolysis | Good growth, no hemolysis |

TABLE 3

| Physiological findings | Bacillus badius IAM 11059 | MA001 |
|---|---|---|
| Grain | Positive | Positive |
| Motility | + | + |
| OF test | | |
| Glucose | No growth | No growth |
| Glycerine | F | No growth |
| Fructose | F | No growth |
| Aerobic growth | + | + |
| Microaerophilic growth | + | + |
| Anaerobic growth | − | − |
| Growth temperature | | |
| 15° C. | + | + |
| 25° C. | + | + |
| 35° C. | + | + |
| 45° C. | + | + |
| 55° C. | − | − |
| Halotolerance | | |
| 0% | + | + |
| 2% | + | + |
| 5% | + | − |
| 7% | + | − |
| 10% | − | − |
| Growth pH | 6.0~9.1 | 6.0~9.1 |

TABLE 4

| Physiological findings | Bacillus badius IAM 11059 | MA001 |
|---|---|---|
| Gelatin decomposition | + | − |
| Starch decomposition | − | − |
| Casein decomposition | + | − |
| Esculin decomposition | − | − |
| Cellulose decomposition | − | − |
| Tyrosine decomposition | + | − |
| Hippuric acid decomposition | − | + |
| Catalase production | + | + |
| Oxydase production | + | + |
| LV reaction | − | No growth |
| Lipase production | − | − |
| DNase production | + | + |
| Urease production (C) | − | − |
| Indole production | − | − |
| VP test: pH 6.5 | − | − |
| VP test: pH 7.5 | − | − |
| Pigment production | + | − |
| Nitrate | | |
| (N) | − | − |
| (NO$_2$) | − | − |
| (NO$_3$) | − | − |
| Utilization | | |
| citrate (S) | − | − |
| citrate (C) | − | + |
| Utilization: malonic acid | + | + |
| Utilization: acetic acid (pH 6.8) | − | − |
| Coagulation test of milk | + | − |
| Purple milk | violet, transparent | violet turbid |
| Protein digestion test | + black | − |
| GC content (HPLC) | 44% | 38% |

Ref:

Urease production (C); Christensen (1946) J. Bcteriol., 52:461,

Citrate (S); Simmons (1926): J. Infect. Dis., 29:209,

Citrate (S); Christensen (1949): Research Bulletin, Greeley, Colo., Weld. County Health Dep., 1:3,

TABLE 5

| Physiological findings | Bacillus badius IAM 11059 | MA001 |
|---|---|---|
| Acid production | | |
| L-Arabinose | − | − |
| D-Fructose | + | − |
| D-Galactose | − | − |
| D-Glucose | − | − |
| Glycerin | + | − |
| Inositole | − | − |
| Lactose | − | − |
| Maltose | − | − |
| D-Mannose | − | − |
| Sorbitol | − | − |
| S. Starch | − | − |
| Sucrose | − | − |
| Trehalose | − | − |
| D-Xylose | − | − |
| Gas formation | | |
| L-Arabinose | − | − |
| D-Fructose | − | − |
| D-Galactose | − | − |
| D-Glucose | − | − |
| Glycerin | − | − |
| Inositole | − | − |
| Lactose | − | − |
| Maltose | − | − |
| D-Mannose | − | − |
| Sorbitol | − | − |
| S. Starch | − | − |
| Sucrose | − | − |
| Trehalose | − | − |
| D-Xylose | − | − |

The above taxonomical findings are referred to "Bergey's Manual of Systematic Bacteriology, 8th Ed., Vol. 2" and "Classification and Identification of Microorganisms" (Hasegawa, Takeji Ed. Gakkai Center Publ.) and the present strain MA001 has found to have similar taxonomical properties of the strain Bacillus badius IAM 11059. However following different properties between the present strain MA001 and Bacillus badius IAM 11059 are observed.

(a) Identical property on 10% defibrinated blood heart infusion agar (added with horse defibrinated blood) showing good growth. However, no growth of the present strain on the medium added with rabbit defibrinated blood and sheep defibrinated blood.

(b) No growth on heart infusion agar added with egg yolk for LV reaction.

(c) No assimilation of sugars.

(d) No decomposition of gelatin.

(e) Different in GC contents.

The above difference indicates that the present strain MA001 differs from the known Bacillus badius. Consequently, the present strain is designated as Bacillus badius MA001 and has been deposited in National institute of Bioscience and Human-Technology, Agency of Industrial Science and Technology, Ministry of International Trade and Industry, Japan as permanent accession No. FERM BP-4493 on Dec. 10, 1993.

Cultivation of the present strain Bacillus badius MA001 can be made without limitation by known culturing methods, for example under aerobic condition in liquid culturing medium containing organic and inorganic nutrients for general microorganisms.

Preferable media are any nutrient medium used in the fermentation technology, for example a medium containing organic nutrients such as bouillon, yeast extract, peptone and bovine brain and heart extracts and inorganic nutrients such as soluble salt which generates ion e.g. sodium, potassium, magnesium, calcium, manganese, cobalt, zinc, iron, chlorine, carbonate, sulfate, nitrate and phosphate. Further organic and inorganic nutrients necessary for growth of microorganisms can be added, if required. For preferable sporulation, sporulation stimulation factor such as potassium ion, magnesium ion or copper ion can be added, or deficient nutrient medium can be used. As shown in the biochemical properties, i.e. utilization of sugar (acid production) in Table 5, utilization of sugar is limited. Therefore, carbon source including lower to medium size chain fatty acid of $C_{1-10}$, preferably $C_{2-8}$, or soluble salt thereof, an offensive odor substance, and nitrogen source such as ammonium salt are preferably used in the medium.

The present strain *Bacillus badius* MA001 having deodorizing activity can be cultured by standing culture and is preferably cultured by liquid culture with direct inoculation. Preferable cultivation is aerobic cuture with shaking the medium.

Culturing temperature can be set up within a range for microbial growth, and is 15°–45° C., preferably 25°–38° C.

The pH of the medium may be controlled within a range of microbial growth and is adjusted to pH 5–10, preferably pH 7–9.

Culturing time depends on a type of medium and its concentration, and is usually 24–100 hours. It may be terminated when sporulation is completed, and is preferably for 36–72 hours, whereby substantially pure cultured microorganism of *Bacillus badius* MA001 can be obtained.

A microbial composition containing substantially pure cultured microorganism strain of *Bacillus badius* MA001 having deodorizing activity as the active ingredient can be prepared by separating microbial cells such as cultured vegetative cells, vegetative cells containing endospore or spores and cells from cultured broth by conventional centrifugation or membrane separation in use of membrane filter to obtain separated cells. Vegetative cells and spores are not necessary to separate.

Spores can be isolated by treating the microbial cells with microbial cell lytic enzyme such as lysozyme to lysate vegetable cells. Spores can also be prepared by sterilizing the vegetative cells, for example sterilization with 70% alcohol or heating at 60°–95° C.

The thus obtained bacterial cells, preferably spores, are washed with water by conventional preparative method for bacterial preparation, suspended in water and concentrated or mixed with diluents or binding agents and dried under condition of not to kill spores to prepare dried cell preparation.

Drying condition can be selected by any method without killing spores, for example lyophilization, aeration drying, spray drying and vacuum drying to prepare dried cells. Formulation of the deodorant microbial composition can be any type of preparation, for example, liquid, powder, granules and tablets. Microbial cells without drying can be used in the form of suspension or paste of cells.

Powdered, granulated or tableted preparation of the dried microbial cells, which are prepared by mixing directly with water absorbent for adjusting water content such as sawdust, zeolite or foaming concrete as a diluent and the microbial cultured mass, or by removing water from the cultured mass, can be used. Additives may not be required if not necessary.

Conventional additives such as diluent, fillers, binders or disintegrators can be used. Examples of water soluble additives are carbohydrate such as dextrose, lactose, cyclodextrin, ologosaccharide and soluble starch, and protein such as albumin and casein or salts. Examples of water insoluble additives are starch, wheat bran, sawdust and bagasse, or natural products including cellulose, chitin or gelatin as a main component, and inorganic products such as calciuim carbonate, calcium sulfate, magnesium carbonate, activated charcoal, white sands, diatomaceous earth and glass. Microbial cells of the present invention can also be immobilized in polymer such as polyacrylamide, vinyl chloride, nylon, urethane and polyester, to prepare preferable form.

Content, of the microbial cells of the present invention in the microbial composition having deodorizing activity, can be adjusted depending upon the deodorant used. For example, the deodorant may be prepared by containing microbial cells of $1\times10^5$–$1\times10^{12}$ cells/g.

Usage of the deodorant of the present invention may be selected in any ways, for example administration by mixing with feeds or suspending in drinking water and directly spraying over or mixing with feces or putrefied organic substances.

Specific offensive odor originated from feces can be reduced by administering to animals by adding the dried microbial cells of *Bacillus badius* MA001 having deodorizing activity or by spreading in excreted feces and urine. Odorous substance is effectively decomposed by leaving for over one day at ambient temperature.

Types of feeds with adding microbial cells of *Bacillus badius* MA001 of the present invention are not limited. Examples of feeds are natural or artificial feeds for animals, for example pets such as dogs and cats, livestock and poultry such as pigs, cattle, chickens, deer, rabbits and goats, animals for experiments such as monkeys, mice, rats and guinea pigs, animals such as elephants and lions, and fishes such as goldfish, eel, sweetfish, salmon, sea bream, young yellow tail and flatfish. Micorbial cells of *Bacillus badius* MA001 of the present invention can be added in the said feeds at any amount.

Amount of addition of the microbial composition of the present invention having deodorizing activity is, in general, the amount of deodorant containing microorganism of over $1\times10^6$ cells per 100 g or the feed. Preferably, sporulated cells of $1\times10^5$–$1\times10^{10}$ cells/g of the feed, and more preferably $5\times10^5$–$5\times10^7$ cells/g of the feed are added. Spreading in the place where marked generation of offensive odoris found, is effectively made, for example $1\times10^5$–$1\times10^{12}$ cells/100 g, i.e. sources of offensive odor, feces or garbage, preferably over $1\times10^5$ cells, more preferably $1\times10^7$–$1\times10^{11}$ cells/100 g of feces or garbage. By considering the amount used hereinabove, the preferable preparation can be prepared.

Deodorizing effect of the present invention on feces or putrefied organic substances can be achieved by decomposing the offensive odorous substances with catabolism and metabolism of the present microbial cells or suppressing the generation of offensive odor by microbial conversion.

Figure 1:
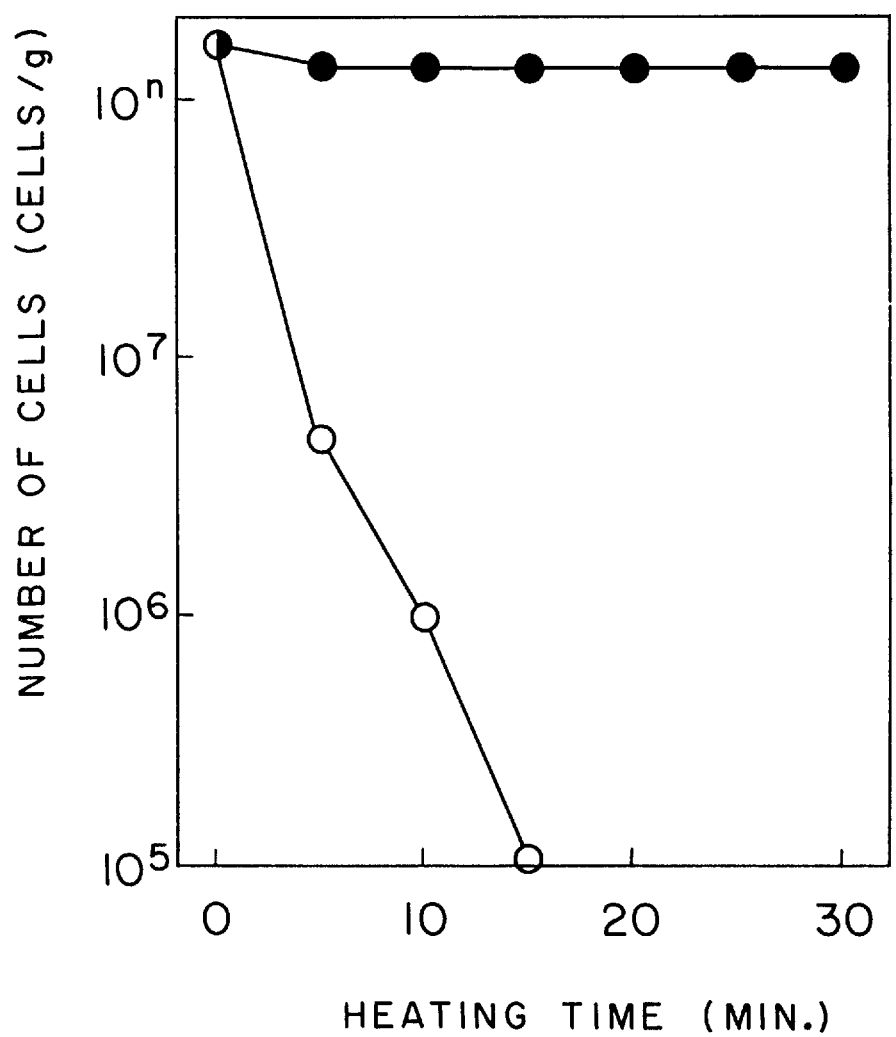
FIG. 1 shows heat stability of *Bacillus badius* MA001 at 80° C.

Following examples illustrate the present invention but are not to be construed as limiting.

EXAMPLE 1

Yeast extract 3 g, peptone 10 g, sodium chloride 5 g, propionic acid 1 ml, n-butyric acid 1 ml and ammonium phosphate 2 g were dissolved in purified water 1000 ml and adjusted to pH 7.5 to prepare liquid medium. Medium was set in 2 lit. jar-fermenter, and *Bacillus badius* MA001 was inoculated therein and cultured at 37° C. for 48 hours to obtain cultured mass. The same composition of the medium was prepared and set in the same size of jar-fermenter, and type culture *Bacillus badius* IAM 11059 was inoculated, then cultured at the same condition hereinabove. Cell counts in each medium were calculated by measuring the optical absorption of the diluted cultured broth, wherein the cultured broth was diluted with purified water and the optical density of the diluent was set to measurable value (O.D. at 660 nm, 1 cm path length) above 2, and being multiplied by dilution number.

Optical density (O.D.) of the cultured medium of *Bacillus badius* MA001 of the present invention was 5.2 and that of the type culture *Bacillus badius* IAM 11059 was 5.0. The cultured broth was observed by microscopy and was confirmed to contain the spores over 80% in the medium. Microbial cells were collected by centrifugation, washed twice with sterilized physiological saline and lyophilized. The lyophilized cells were mixed with equivalent weight of calcium carbonate powder to prepare powdered microbial cell composition.

Deodorizing effect and preventive effect for offensive odor of porcine feces were measured using these cell compositions (viable microbial cell number approx. $10^{11}$ cells/g). Deodorizing effect was evaluated by sensory test. The sensory evaluation was performed by 7 panelists, and was decided according to the following 6 degree offensive odor grading method and 9 degree pleasure-displeasure expression method. Each sensory evaluation was performed according to "Method of sensory test for offensive odor"—Manual for measuring by three points comparative odor bag method—, published by Assoc. for countermeasure on odor.

[Six grade odor grading expression]

0: not odorous
1: odor barely sensible
2: weakly sensible odor
3: easily sensible odor
4: strong odor
5: intense odor

[Nine degree pleasure-displeasure expression]

−4: intensively unpleasant
−3: very unpleasant
−2: unpleasant
−1: slightly unpleasant
0: not so pleasant and not so unpleasant
+1: slightly pleasant
+2: pleasant
+3: very pleasant
+4: intensively pleasant Fresh porcine feces were weighted 100 g in a beaker. Three sets of feces in beaker were set up. Powdered microbial cell preparation 1 g of *Bacillus badius* MA001 of the present invention, that of type culture strain *Bacillus badius* IAM 11059, and calcium carbonate powder 1 g, respectively, were added and mixed. Each beaker was sealed with aluminium foil and allowed to stand at 30° C. Changes of odor of porcine feces at every 12 hours were observed for 3 days. Results were shown in Table 6 (Six grade odor grading expression) and Table 7 (Nine grade pleasure-displeasure expression).

TABLE 6

| Test | Measuring time (hour) | | | | | | |
|---|---|---|---|---|---|---|---|
| | 0 | 12 | 24 | 36 | 48 | 60 | 72 |
| No addition | 4 | 5 | 5 | 5 | 5 | 4 | 4 |
| MA001 | 4 | 3 | 3 | 2 | 2 | 1 | 1 |
| IAM 11059 | 4 | 5 | 5 | 5 | 4 | 4 | 4 |

TABLE 7

| Test | Measuring time (hour) | | | | | | |
|---|---|---|---|---|---|---|---|
| | 0 | 12 | 24 | 36 | 48 | 60 | 72 |
| No addition | −3 | −3 | −3 | −4 | −4 | −4 | −4 |
| MA001 | −3 | −3 | −2 | −2 | −1 | 0 | 0 |
| IAM 11059 | −3 | −3 | −3 | −3 | −4 | −4 | −4 |

Results shown in Tables 6 and 7 indicated that no deodorizing effect was observed without difference as compared with no addition control group after 72 hours in the type culture strain *Bacillus badius* IAM 11059, and deodorizing effect was observed after 12 hours in *Bacillus badius* MA001 of the present invention, in which clear difference of offensive odor of porcine feces as compared with no addition control and type culture strain *Bacillus badius* IAM 11059. Offensive odor of the sample in the beaker added with *Bacillus badius* MA001 almost disappeared at 48 hours.

Test group of the type culture strain *Bacillus badius* IAM 11059 and control group of calcium carbonate powder generated offensive oder over 3 weeks. No offensive odor was observed in the beaker added with *Bacillus badius* MA001 which was allowed to stand thereafter at 30° C., and deodorizing effect was observed over 3 months.

EXAMPLE 2

Microbial cells of *Bacillus badius* MA001 containing spores, for which microbial cells in cultured medium were microscopically observed and spores were observed more than 80% in the microscopic field, were obtained by cultivation for 48 hours in the same manner as of in Example 1. Microbial cells without sporulation of *Bacillus badius* MA001 were obtained by cultivation for 18 hours, for which cultured cells were observed microscopically to confirm no sporulation and whole vegetative cells, were also obtained.

Microbial cells were collected by centrifugation and suspended in sterilized water. Ten ml of the suspension in test tube were heated in water bath at 80° C. for 30 minutes. Each sample collected every 5 min. was diluted with water and spread on the heart infusion agar plate to count number of viable cells.

Result is shown in FIG. 1. Sporulated cells of *Bacillus badius* MA001 were very stable under heating at 80° C. In FIG. 1: ●: sporulated cells, ○: non sporulated cells. No difference on deodorizing effect was observed.

EXAMPLE 3

Fresh feces 200 g obtained from pigs reared by standard test feed for pigs (Nippon Formula Feeds Co., standard test feed for pigs SDS No. 4) were mixed well with purified water 800 ml. The mixture was adjusted to pH 7.5 by adding 1N—HCl and 1N—NaOH to prepare 20% feces solution. The feces solution of each 100 ml were dividedly put into 500 ml Erlenmeyer flasks, cotton sealed and sterilized at 121° C. for 20 minutes by autoclave.

Two flasks containing feces solution of pigs were selected, and the one of which was inoculated with *Bacillus badius* MA001 and the other of which was set to the control without inoculation. These flasks were shake cultured at 37° C. for 12 hours and 24 hours. Each point of cultivation at hour 0, hour 12 and hour 24, respectively, odor was detected for the testing group and the control group. Sensory tests were evaluated by the same way as of in Example 1 by 7 panelists according to the 6 grade odor grading expression. Result is shown in Table 8, in which odor in the testing flask was decreased after 12 hours and completely deodorized after 24 hours.

TABLE 8

|  | Hour 0 | Hour 12 | Hour 24 |
|---|---|---|---|
| Control | 5 | 5 | 5 |
| Test | 5 | 2 | 0 |

One ml of cultured mass obtained from 24 hours cultivation was diluted with purified water 9 ml to prepare a solution of 10 fold-dilution, for which detection of ammonia was examined in the 24 hours cultured mass. Two drops of Nessler reagent was added thereto and mixed well. The 10 fold dilution of the cultured mass in the control flask became turbid to indicate existing ammoniuim ion. On the contrary, the 10 fold dilution of the cultured mass in the test flask, for which the strain MA001 having deodorizing activity was inoculated, remained with transparency to be detected no ammonium ion.

Lower fatty acid in the cultured mass in each flask was detected by gas-chromatography in order to compare amount of fatty acid of offensive odor sources in the cultured mass in case with or without inoculation of the microorganism strain of the present invention. Cultured mass was centrifuged at 3000 rpm for 15 min. to obtain cultured filtrate. 10 ml of the cultured filtrate was adjusted to pH 1.0 by adding hydrochloric acid. 10 ml of diethyl ether were added thereto to transfer lower fatty acid to the diethyl ether. Fatty acid was methylated by diazomethane, and analyzed in use of gas chromatography (column: polyethylene glycol 1500, 2.1 m, 60–80 mesh, detector: flame ionization detector, carrier gas: $He_2$ 0.5 $kg/cm^2$, fuel gas $H_2$ 0.5 $kg/cm^2$, air: 0.5 $kg/cm^2$).

Result is shown in Table 9, in which gas chromatographic analysis of lower fatty acid contents in feces within 24 hours (measured value in the control is set to 100%) is indicated. Lower fatty acid in the culture filtrate obtained from inoculation of the deodorant bacterium of the present invention was decreased in time dependently and effectively deodorized.

TABLE 9

|  |  | Hour 0 | Hour 12 | Hour 24 |
|---|---|---|---|---|
| Control | propionic acid | 100 | 100 | 100 |
|  | n-butyric acid | 100 | 100 | 100 |
|  | iso-valeric acid | 100 | 100 | 100 |
|  | n-valeric acid | 100 | 100 | 100 |
| Test | propionic acid | 100 | 86 | 16 |
|  | n-butyric acid | 100 | 56 | 9 |
|  | iso-valeric acid | 100 | 22 | 20 |
|  | n-valeric acid | 100 | 23 | 22 |

EXAMPLE 4

Yeast extract 2 g, sodium chloride 5 g, propionic acid 1 ml, n-butyric acid 1 ml, iso-valeric acid 1 ml, n-valeric acid 1 ml. ammonium phosphate 2 g, indol 10 mg and trimethylamine 1 ml were dissolved in 1000 ml of purified water and adjusted to pH 7.5 to prepare a liquid medium. The liquid medium 100 ml was dividedly set in 500 ml culture flask, sealed with cotton plug and autoclaved at 121° C. for 20 minutes. *Bacillus badius* MA001 of the present invention and *Bacillus badius* IAM 11059, each one loopful, were inoculated and cultured at 37° C. for 36 hours in at 150 rpm.

Figure 2:
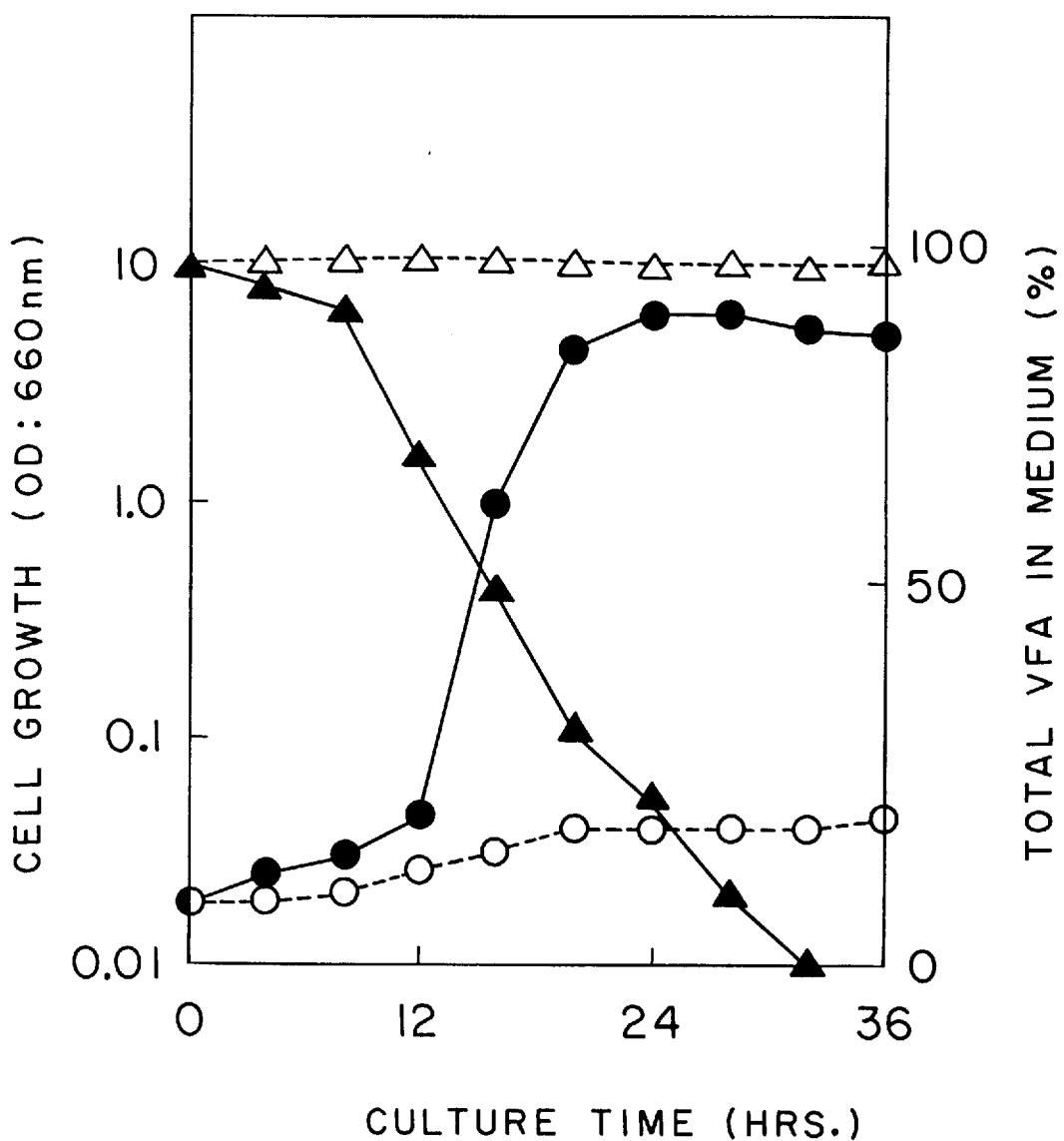
FIG. 2 shows growth curve of *Bacillus badius* MA001 and type culture *Bacillus badius* IAM 11059 and total lower fatty acid (VFA) in medium.

Bacterial growth by cultivation was observed time dependently by measuring optical density of the cultured mass by the same way as described in Example 1 (O.D.: 660 nm. 1 cm path length). Levels of lower fatty acid in cultured medium was measured at the growth of bacteria. Growth of bacteria and assimilation of lower fatty acid on both strains were compared. Fatty acid in the medium was measured by the same method as described in Example 3. As shown in FIG. 2, in which ●: growth of *Bacillus badius* MA001; ○: growth of type culture strain *Bacillus badius* IAM 11059; ▲: total fatty acid in cultured *Bacillus badius* MA001; and Δ: total fatty acid in type culture strain *Bacillus badius* IAM 11059, *Bacillus badius* MA001 of the present invention showed good growth, good assimilation of lower fatty acid in the medium and effective deodorization as compared with the type culture strain *Bacillus badius* IAM 11059.

Ammonium ion in the medium cultured for 36 hours was measured. The ammonium ion in the cultured mass was detected by adding Nessler reagent by the same way as described in Example 1. The 10 fold dilution of cultured mass of type culture Bacillus 00adius IAM 11059 became turbid with red brownish color to indicate existence of high concentration of ammonium ion. The 10 fold dilution of cultured mass of *Bacillus badius* MA001 of the present invention showed light orange color which indicated existence of trace ammonium ion. Therefore, the strain *Bacillus badius* MA001 was shown as low ammonium producing strain having low productivity of ammonia in the medium under cultuvation.

Assimilability of indole added to the medium was also examined. Cultured mass was centrifuged at 3000 rpm for 15 minutes to obtain supernatant liquid. VanUrk reagent 1.5 ml was added in the supernatant 1.5 ml and colorimetrically measured at 578 nm after 10 minutes. Trace indole was detected in the type culture strain *Bacillus badius* IAM 11059 with indicating slight pinkish color of VanUrk reagent. On the contrary no indole was detected in *Bacillus badius* MA001 of the present invention. Although further odor of indole in the cultured mass was inspected by sensory testing, no odor of indole was detected after cultivation with showing effective deodorization of indole odor.

Detection of trimethylamine was conducted as follows. Cultured mass 5 ml was added in a test tube, and formalin (not diluted) 1.5 ml was added and mixed well, allowed to stand for 3 min., then aqueous saturated potassium carbonate 3 ml was added thereto, thereafter immediately sealed with rubber stopper which has small size of hole attached with a cotton swab, length about 3 cm. The cotton swab was previously immersed with bromthymol blue solution adjusted to pH 4.0 by 1N-sulfuric acid. The test tube was set in water bath at 45° C. or 15 minutes, whereby if trimethylamine was present in the medium, the immersed bromthymol blue would be changed to blue by an action of vapourized trimethylamine. No trimethylamine was detected in the medium of *Bacillus badius* MA001 of the present invention according to the test method hereinabove. Also no odor of trimethylamine in the medium was found to indicate effective deodorization of trimethylamine.

EXAMPLE 5

Yeast extract 2 g, sodium chloride 5 g, propionic acid 1 ml, n-butyric acid 1 ml, iso-valeric acid 1 ml, n-valeric acid 1 ml, ammonium phosphate 2 g and skatole 10 mg were dissolved in 1000 ml of purified water and adjusted to pH 7.5 to prepare a liquid medium. The liquid medium 100 ml was dividedly set in 500 ml culture flask, sealed with cotton plug and autoclaved at 121° C. for 20 minutes. *Bacillus badius* MA001 of the present invention and *Bacillus badius* IAM 11059, each one loopful, were inoculated and cultured at 37° C. for 36 hours in 150 rpm.

VanUrk reagent was added to the cultured mass 15 ml in test tube and colorimetrically measured at 578 nm after 10 minutes. Trace skatole was detected in the type culture strain *Bacillus badius* IAM 11059 with indicating slight pinkish color of VanUrk reagent. On the contrary no skatole was detected in *Bacillus badius* MA001 of the present invention. Odor of skatole in the cultured mass of *Bacillus badius* MA001 was inspected by sensory testing, and no odor of skatole was detected after cultivation.

EXAMPLE 6

Fresh feces 100 g obtained from pigs, 10 weeks age, grown with normal rearing were set in a 500 ml glass beaker. Liquid cultured mass 5 ml of *Bacillus badius* MA001 cultured for 48 hours same way as described in Example 1 was added therein and mixed well. Similar fresh feces of pigs 100 g were set in a 500 ml beaker, added sterilized water 5 ml thereto to prepare control group.

Offensive odor of the procine feces cultured at 30° C. in the same way as described in Example 1 was evaluated by 7 panelists once a day for 7 days. The sensory test was conducted by direct sniffing of feces and evaluated by the six grade odor expression method. As shown in Table 10, decrease in specific odor of porcine feces on the day 1 in the test group added with the microbial composition was found, and no offensive odor was detected from the day 3.

TABLE 10

| Test | Day 0 | Day 1 | Day 2 | Day 3 |
|---|---|---|---|---|
| Control | 5 | 5 | 5 | 5 |
| MA001 | 5 | 3 | 2 | 2 |
| | Day 4 | Day 5 | Day 6 | Day 7 |
| Control | 4 | 4 | 5 | 5 |
| MA001 | 1 | 1 | 0 | 0 |

EXAMPLE 7

Rats were bred at 22° C. (±0.5° C.) supplying ad libidim with water and pellet feed for rats (CE-2, Nihon Clea Co.) for 1 week and no abnormal appearance and behavior were observed. Three test groups consisting of 10 rats (SD rats: Nihon Clea Co., male, body weight 200 g at the introduction date) in one group in the cage were set up.

Samples 2 ml hereinbelow defined were administered orally once in a day for 3 weeks. Acute toxicity test observing with mortality, growth, behavior and appearance was conducted.

Test samples were as follows. Sample 1: cultured mass of *Bacillus badius* MA001 cultured by the same way as described in Example 1; Sample 2: microbial cells of *Bacillus badius* MA001 cultured by the same way as described in Example 1 were collected and washed twice with sterilized physiological saline. Equivalent weight of the sterilized physiological saline was added to the wet cells to prepare 50% cell suspension; and Sample 3: control with sterilized physiological saline.

No death was observed in any 3 groups tested. No abnormalities in feces and urine (color, diarrhea and bloody stool), saliva (salivation, serosity and mucus), respiration, nutriture (weakness, weight-loss and weight-gain), nose and mouth (nose bleed, trace of nose bleed, nasal discharge and mouth smudge), anus (smudge and rectal prolapse), activity, movement and emotion were observed.

No abnormal weight changes were observed as compared with the control group administered with the sample 3.

As a results of dissection of the rats, no abnormal findings in organs (liver and kidneys) and degestive organs (stomach, intestine, cecum and colon) were observed.

No acute toxicity and side effect of microbial cells and cultured mass of *Bacillus badius* MA001 were found.

EXAMPLE 8

Ten pigs (landrace, male), weight 80 kg, were divided into two groups of test group and control group, each consisting of 5 pigs.

Rearing were conducted as follows: windowless piggery, single rearing, ventilation by fan, slotted floor and feces accumulated below the slotted floor. Feeding was made on the first 2 weeks with standard feed for pigs (Nihon Formula Feed Co., Test feed for pork pigs SDS No. 4) and thereafter commercially available feed added with feed additives (Zenno Corp.).

Feeds were administered ad libidim and were kept to remain at any times in feed box. Water was supplied ad libidim. In the test group, powdered microbial cells of *Bacillus badius* MA001 prepared as the same way as described in Example 1, $10^6$ cells/g of feed, were supplied. In the control group, microbial cell powder in the test group was replaced by calcium carbonate.

Odor in the piggery and below the slotted floor was evaluated once in a week by 7 panelists according to the same method as described in Example 1. Results are shown in Table 11 (six grade odor grading expression) and Table 12 (nine grade pleasure-displeasure expression). Test group supplied with powdered composition of *Bacillus badius* MA001 of the present invention showed extreme decrease in offensive odor and unpleasant atmosphere as compared with the control group, and the effect was unchanged after changing the feeds.

TABLE 11

|  |  | Start | Week 1 | Week 2 | Week 3 |
|---|---|---|---|---|---|
| Control | Rearing room | 4 | 4 | 4 | 4 |
|  | Slotted floor | 4 | 4 | 5 | 5 |
| Test | Rearing room | 4 | 2 | 1 | 1 |
|  | Slotted floor | 4 | 2 | 2 | 1 |

TABLE 12

|  |  | Start | Week 1 | Week 2 | Week 3 |
|---|---|---|---|---|---|
| Control | Rearing room | −3 | −3 | −3 | −3 |
|  | Slotted floor | −3 | −4 | −4 | −4 |
| Test | Rearing room | −3 | −1 | −1 | −1 |
|  | Slotted floor | −3 | −2 | −1 | −1 |

Sensory tests were exactly conducted according to "the sensory test method for odor"—Manual for testing odor bag three point comparative method—published by Assoc. of Research Corp. for Odor. Odor concentration was assessed by odor bag three point assessment by 7 panelists. Result is shown in Table 13. Details of test method are as follows. Odor was diluted in the 3 lit. polyester bag (odor bag) for test group and non-odorous fresh air was set in the same size bag. Any three bags thereof were assessed on the points of odor (odorous or not odorous) by the panelists. Assessments were continued until obtaining the same degree of odor concentration of the non odorous bag by diluting with fresh air. Table 13 shows number of dilution of the odor. Odor concentration: A method of quantification of odor. Number of dilution at the point of not to feel odor when the odor is diluted with fresh air is defined as odor concentration. (Ed. supervison by Environmental Pollution Dept., Air Quality Bureau, Environment Agency "Terms and commentary on odor", published by Assoc. of Research Corp. for odor, Mar. 31, 1990)

TABLE 13

|  |  | Start | Week 1 | Week 2 | Week 3 |
|---|---|---|---|---|---|
| Control | Rearing room | 30 | 50 | 50 | 75 |
|  | Slotted floor | 75 | 125 | 200 | 200 |
| Test | Rearing room | 30 | 20 | 4 | 2 |
|  | Slotted floor | 75 | 30 | 10 | 5 |

Oral administration of powdered microbial cells of *Bacillus badius* MA001 with feed in pigs showed marked deodorizing effect for environmental odor in piggery.

EXAMPLE 9

A model sample of garbage was prepared. Mixture of tofu (bean-curd) refuse 100 g at the tofu production, finely cut strips of onions 25 g, boiled fine noodles 25 g and minced pork 25 g was put in 2 lit. beaker, covered with aluminium foil and allow to stand at room temperature for 1 week. The putrefied garbage model with extreme offensive odor was pressed to remove water through gauze. 100 g thereof was put in 1 lit. beaker and mixed well with powdered microbial cells of *Bacillus badius* MA001 3 g prepared by the same method as described in Example 1, and incubated at 30° C. Positive aeration was made by mixing the content once in a day. Assessment of deodorizing effect was performed by once a day sensory evaluation on the putrefied garbage in the beaker by the same way as described in Example 1 to examine generation of odor. Decrease in offensive odor after 1 day, and no strong offensive odor were found after 3 days. Offensive odor was not found after 6 days.

REFERENTIAL EXAMPLE 1

Preparation of non odorous compost

Compost was prepared using porcine feces 20 kg bred with the same condition as described in Example 6 (microbial composition of the present invention was added). Sawdust was mixed with feces to adjust water content at 60%, and fermented to prepare compost. Fully fermented compost was prepared within 30–35 days, whereas conventionally required for 6 months to 1 year.

After 24 hours of fermentation started, rapid decrease of odor was found. On the third day, almost no odor was felt and on the 7th day no odor was found. The compost showed odorless over 3 months. Fully fermented compost was dried and was seen without giving dirty feeling. No offensive odor was observed when the compost was suspended with water.

Effect of the invention

Application of vegetative cells of *Bacillus badius* MA001 having deodorizing activity of the present invention, vegetative cells having endospores or spores and cultured mass containing the same, on odor sources resulted in good growth by assimilating with odorous substances in the organic sewage to show and continue deodorizing effect. It is effective for deodorizing garbage can, toilet, feces and urine and putrefied feed from animal industries, feces and urine of pets, fish odor of fishing nets, air-filter, sewage water and sewage plants.

Deodorant of the present invention can be applied for reducing odor by direct spread of the microbial cells or cultured mass on offensive odor sources, or by setting the immobilized microbial cells or cultured mass on the deodorizer filters and deodorizing devices.

In the case that offensive odor sources are feces and urine of animals, oral administration of feed added with deodorizing microorganisms of the present invention can reduce odor of the excretion of the animals, as well as being effective for offensive odor sources generated from feces and urine or putrefied feeds adhered to the barn, and liquid swege drains, transportaion route of feces and urine or treatment plant therefor.

Feces and urine added with the present microorganism reduces generation of offensive odor such as ammonia in the manufacture of compost and are changed to odorless compost.

No toxicity and side effect of the present microorganism are observed, therefore continuous spray of administration can be possible as well as suppressing generation of offensive odor. Deodorant of the present invention has made it possible to provide very effective and reliable countermeasure for treatment of offensive odor in atmosphere of rearing animals and animal industries and sewage plants. The present invention also makes it possible to provide to suppress animal odor or to prevent adhering odor to the products such as eggs and milk by improving rearing circumstances.

What is claimed is:

1. A biologically pure culture of strain *Bacillus badius* FERM BP-4493 having deodorizing activity for an odorous substance, said strain being capable of producing spores.

2. The strain according to claim 1, wherein the odorous substance is selected from the group consisting of a fatty acid of approximately 1–10 carbon atoms, ammonia, indole, skatole and trimethylamine.

3. The strain according to claim 1, having low productivity of ammonia in a culture medium.

* * * * *